(12) United States Patent
Agur et al.

(10) Patent No.: US 8,762,069 B2
(45) Date of Patent: Jun. 24, 2014

(54) THERAPEUTIC IMPLICATIONS OF DICKKOPF AFFECTING CANCER STEM CELL FATE

(75) Inventors: Zvia Agur, Tel Aviv (IL); Oleg U. Kirnasovsky, Petach Tikva (IL); Yuri Kogan, Jerusalem (IL); Lilach Tencer, Rehovot (IL)

(73) Assignee: Institute for Medical Biomathematics, Bene Ataroth (IL)

( * ) Notice: Subject to any disclaimer, the term of this patent is extended or adjusted under 35 U.S.C. 154(b) by 403 days.

(21) Appl. No.: 12/721,968

(22) Filed: Mar. 11, 2010

(65) Prior Publication Data

US 2010/0235150 A1 Sep. 16, 2010

Related U.S. Application Data

(60) Provisional application No. 61/159,123, filed on Mar. 11, 2009.

(51) Int. Cl.
  *G06F 19/00* (2011.01)
  *G06G 7/58* (2006.01)
(52) U.S. Cl.
  USPC .............................................. 702/19; 703/11
(58) Field of Classification Search
  CPC ..... G06F 19/12; G06F 19/34; G06F 19/3437; G01N 33/50; G01N 33/68; G01N 2500/04
  See application file for complete search history.

(56) References Cited

U.S. PATENT DOCUMENTS

2005/0130192 A1* 6/2005 Paterson et al. .................... 435/6
2007/0231325 A1* 10/2007 Clarke et al. ............... 424/138.1

OTHER PUBLICATIONS

Agur et al. Biol. Direct (2012) vol. 444, pp. 115-125.*
Kogan et al. Biochem. J. (2012) vol. 5, pp. 1-11.*
Katoh and Katoh (Clinical Cancer Research (2007) vol. 13(14):4042-4045; herinafter "Katoh").*
Prudhomme et al. PNAS (2004) vol. 101, pp. 2900-2905.*
Qiao et al. Cancer Letters (2008) vol. 269, pp. 67-77.*

* cited by examiner

*Primary Examiner* — Lori A Clow
(74) *Attorney, Agent, or Firm* — Sughrue Mion, PLLC (57) ABSTRACT

A method of determining a therapeutic regimen for the treatment of cancer with Dickkopf (Dkk) protein in which a mathematical model of differential equations describing the major signaling pathways involved in stem cell regulation is created and used to simulate signals from the cancer stem cell environment based upon administration of at least a single dose of Dkk in vitro and/or in vivo. A method of modulating cancer stem cells is also provided in which the stem cell computer model is simulates the effect of Dkk and performs a calibration test to determine a threshold value above which Dkk induces cell differentiation and a threshold value below which Dkk induces stem cell proliferation.

25 Claims, 4 Drawing Sheets

| Mutation | Secreted Dkk/SC |
|---|---|
| No mutation | 31.88 |
| Notch + 5% | 31.51 |
| Notch + 10% | 30.69 |
| Notch + 15% | 29.74 |
| Wnt + 5% | 32.08 |
| Wnt + 10% | 32.23 |
| Wnt + 15% | 32.40 |

FIG. 4

THERAPEUTIC IMPLICATIONS OF DICKKOPF AFFECTING CANCER STEM CELL FATE

This Application claims benefit of U.S. Provisional Patent Application Ser. No. 61/159,123 filed Mar. 11, 2009, the contents of which are incorporated herein by reference.

A. TECHNICAL FIELD

Breast cancer is the most prevalent cancer among women worldwide and current therapies still fall short of providing effective remission and diminished risk of recurrence. Recent studies, implicating the involvement of Cancer Stem Cells (CSCs) in sustaining tumor growth and recurrence, and the finding that CSCs can escape conventional therapy, underline the difficulty in curing this pathology. However, novel therapy avenues can be uncovered by deciphering the molecular mechanism governing CSCs fate decisions, and by understanding how to divert cellular proliferating into differentiation. The fate of Mammary Stem Cells (SCs) is controlled by complex inter-relationships between several signaling pathways, notably Wnt and Notch. The Dickkopf (Dkk) protein family is a target of the Wnt signaling pathway and several members of this family negatively regulate the Wnt pathway's activity. The Wnt signaling pathway crosstalks with the Notch signaling pathway, which is regulated by the Delta, Serrate, Lag-2 (DSL) ligand. The aim of the present invention is to study these complex interactions and to identify the crucial factor, whose modulation can redirect CSCs into final differentiation. This is accomplished by mathematically analyzing the involved dynamics, which may be intractable to experimental investigation. The mathematical model is a system of seven differential equations describing the major signaling pathways governing SCs development and their interactions. Using this model, the effect of Dkk application on normal SCs proliferation and on that of mammary CSCs was numerically simulated. The simulation results suggest a biphasic effect for Dkk on SCs: Low Dkk levels (within a narrow range) accelerate SC proliferation, whereas high Dkk levels (above a certain threshold) drive SCs into differentiation. Therefore, high Dkk levels may drive CSCs into differentiation leading to tumor elimination. The results also suggest that a continuous application for 48 hours of a sufficiently high Dkk dose leads to a complete SC elimination.

B. BACKGROUND

Breast cancer is the most prevalent cancer among women worldwide [Parkin D M et al, CA Cancer 1⁻ Clin. 55(2):74-108 (2005)]. To date conventional therapies for breast cancer such as surgery, chemotherapy and radiotherapy resulting in effective remission and diminishing risk of recurrence are still lacking. In the past few years accumulated data has indicated many solid tumors to be induced by cancer stem cells (CSCs) located within the tumor, denoted as "side population". These side populations preserve their capacity to proliferate and undergo self renewal [Seo D C et al, Mol Cancer, 6(1):75 (2007)]. In breast cancer cell lines (2%) of the cells suspected as CSCs [Kopper and Hajdu, Pathol Oncol Res. 10(2):69-73 (2004)]. CSCs are difficult to treat due to the unique features they comprise. The CSCs contain an increased number of multi-drug resistant transporter proteins which pump out chemotherapeutic drugs from the cells. This characteristic is manifested by the pumping out of Hoechst 33342 and Rhodamine-123 dies from the cells. Also, the CSCs were shown to be more resistance to radiation [Woodward W A et al, 1⁻ Cell Sci. 118 (Pt 16): 3585-94 (2005)]. Thus, understanding the molecular mechanisms governing CSCs fate decisions may allow for their divergence from proliferation to differentiation.

Two main signaling pathways have been suggested to play an essential role in inducing tumorigenicity in mammary cancer stem cells, the Wnt and the Notch signaling pathways. The Wnt signaling pathway has been suggested to play a role in oncogenesis of numerous types of cancers including colon, leukemia, melanoma and breast [Reya T and Clevers H Nature 434, 843-850, (2005), Brennan K R and Brown A M, J. Mammary Gland Biol. Neoplasia 9, 119-131 (2004)]. The Wnt signaling pathway is initiated by the binding of Wnt ligands to the Frizzled/LRP transmembrane receptors. As a result, the complex Axin/APC/GSK3beta which is involved in beta catenin degradation is inhibited resulting in beta catenin translocation and accumulation in the nucleus. Beta catenin together with the transcription factors LEF/TCF bind to the target genes promoters and induces transcription of genes such as cyclin D1 and c-myc which induce cell proliferation. In the absence of nuclear beta catenin, LEF/TCF, the transcription repressor Groucho and the histone deacetylases comprise a transcription repressive complex that acts to repress the expression of the Wnt target genes which may lead to cellular Differentiation.

The Wnt signaling pathway is modulated by the Dickkopf (Dkk) family proteins. Dkk family proteins consist of 4 members (Dkk1 to Dkk4). Dkk1, Dkk2 and Dkk4 have been previously suggested to play a predominantly inhibitory role in the regulation of the Wnt pathway and increase cell differentiation [Aguilera O et al, Carcinogenesis, 28(9):1877-84 (2007)]. However, recently accumulated data have indicated that Dkk2 may in fact activate the Wnt pathway [Niehrs C, Oncogene 25, 7469-7481 (2006)] and/or induce cell proliferation [Gregory C et al, J Biol Chem, 278(30):28067-78 (2003)]. In the canonical mechanism Dkk1 binds the LRP5/6 receptor at the plasma membrane, induces its internalization and thus prevents the binding of Wnt to the receptor [Niehrs C, Oncogene, 25, 7469-7481 (2006)], which results in Wnt signaling pathway inhibition.

In the recent years, large body of evidence has indicated Dkk family genes as tumor suppressor genes. Dkk are frequently silenced due to promoter hypermethylation in cancer cell lines such as gastrointestinal and other tumors [Sato H, Carcinogenesis, 28(12):2459-66 (2007)]. Moreover, ectopic expression of Dkk in various cancer cell lines resulted in sensitization to apoptosis [Mikheev A M et al Biochem Biophys Res Commun. 352(3):675-80 (2007), Mikheev A M et al Carcinogenesis 25(1):47-59 (2004)]. Ectopic expression of Dkk was also shown to reduced tumorigenity of cancer cell lines [Mikheev A M, et al, Carcinogenesis 25(1):47-59 (2004)].

Another major signaling pathway involves in cancer stem cell is the Notch pathway. Following the binding of Delta, Serrate, Lag-2 (DSL) ligand to Notch receptor, Notch receptor is undergone a series of proteolitic cleavages by several metalloproteases such as, A Disintegrin And Metalloproteinase (ADAM), ADAM 10 and ADAM 17, resulting in the release of Notch intracellular domain (NICD). NICD fragment translocates to the nucleus, where it up-regulates gene expression such as Hes and Hey [Wu F et al, Front Biosci, 12:4370-83 (2007)]. Notch signaling pathway can be inhibited by Numb which binds the intracellular domain of Notch receptor leading to its recruitment into endocytic vesicles [Berdnik D et al, Dev. Cell, 3 (2):221-31 (2002)].

The Notch and the Wnt signaling pathways are cross-talk. In the promoter region of Numb two TCF/LEF binding sites have discovered and thus it was suggested to be a target for the Wnt pathway [Katoh M and Katoh M, Int J Mol Med. 18(3): 517-21 (2006)]. In addition, activation of LEF/TCF up-regulate the Notch ligand Jag 1 (Katoh M and Katoh M Int J Mol Med, 17(4):681-5 2006).

Another important aspect concerning cancer stem cells is the effect of cell-cell contact formed by the adhesion molecule E-cadherin. Changes in E-cadherins expression may indicate cell condition. During cell differentiation the expression of E-cadherins is enhanced whereas deregulation of E-cadherins has been linked to lose of tissue organization and carcinogenesis. E-cadherin influences other signaling pathways such as the Wnt pathway: E-cadherin is connected to the cytoskeleton via beta catenin, which has a pivotal role in inducing cell proliferation as mentioned above, and thus represses transcription initiation, induced by the beta catenin/LEF/TCF complex.

Biological systems include complex interactions and relationships. This complexity often disturbs concise and accurate analysis of test results. Regarding the present invention, CSCs are hard to isolate and identify. Moreover, the role of SCs in solid tumors is controversial and the understanding of universal laws concerning SCs proliferation are lacking. Thus, in silico experimentations using mathematical models may overcome these shortcomings in the study of CSCs, the factors governing their cellular fate and their involvement in tumor formation, progression and recurrence.

In [Agur Z et al, J. Math. Biol. 44, 79-86 (2002), Agur Z et al, a simple discrete model for a developing tissue was put forward and analyzed. Analysis of this model, which is represented by cellular automata on a connected, locally finite undirected graph, shows the minimal number of basic properties responsible for maintaining tissue homeostasis and guaranteeing the ability of a few stem cells to repopulate the tissue after severe perturbations. Thus it is proven theoretically that a Quorum Sensing type of control, that is, regulation of proliferation/differentiation balance by a negative feedback of SCs on their own proliferation, suffices for ensuring homeostasis both in normal and in pathological tissues. However, the molecular mechanism underlying this control still remains to be investigated.

The present invention is aimed at elucidating the molecular mechanism governing SCs and CSCs fate decisions and to identify the crucial factor, whose modulation can divert them into final differentiation. A mathematical model was constructed illustrating the major signaling pathways involved in mammary CSCs cell fate. Moreover, the mathematical model integrates also signals from the CSCs environment. Mathematical analysis of this model shows that SC niche can be formed spontaneously in the tissue, rather than requiring external delimiting structures, as is currently thought [Kirnasovsky O. U, et al Math. Model. Nat. Phenom. 3, 7, 78-89 (2008)]. Moreover, the previous assertion that homeostasis in developing tissues is mainly controlled by a negative feedback on SCs proliferation, denoted Quorum Sensing, is substantiated by this analysis, singling out the Dkk signal in the Wnt pathway as the Quorum Sensing "counter." The analysis further suggests the relative dominance of the involved biochemical pathways in different tissue conditions.

C. SUMMARY OF THE INVENTION

The present invention is directed to a method of modulating cancer stem cells comprising creating a stem cell computer model for at least one signaling pathway involved in stem cell development, comprising a proliferated stem cell (SC) compartment and a differentiated cell (DC) compartment; simulating an effect on the at least one pathway of the stem cell computer model is based upon administration of at least a single dose of Dickkopf (Dkk) protein in vitro or in vivo; performing a calibration test to determine a threshold value above which Dkk induces cell differentiation and a threshold value below which Dkk induces stem cell proliferation.

In a specific embodiment, the signaling pathway is selected from the group consisting of Wnt pathway and Notch pathway.

In another specific embodiment, administration of a Wnt ligand activates the Wnt pathway by binding to a LRP transmembrane receptor.

In another specific embodiment, the binding of a Wnt ligand to a LRP transmembrane receptor activates LEF/TCF transcription complex upon the binding of beta catenin to LEF/TCF transcription complex.

In another specific embodiment, the LEF/TCF transcription complex up-regulates proliferation factors to induce the expression of Wnt target genes that induce cellular proliferation.

In another specific embodiment, the activation of LEF/TCF transcription complex up-regulates Dkk as a negative feedback loop.

In another specific embodiment, activation of LEF/TCF transcription complex is inhibited by Dkk to repress the expression of Wnt target genes to induce cellular differentiation.

In another specific embodiment, activation of LEF/TCF transcription complex is inhibited by E-cadherin.

In another specific embodiment, the binding of a Notch ligand activates the Notch pathway to up-regulate a Notch target.

In another specific embodiment, the Notch ligand is a DSL ligand and the Notch target is Hes. The binding of a DSL to a Notch receptor activates Hes. Hes suppresses synthesis of at least one differentiation factor (DF) in SC.

In another specific embodiment, the differentiation factor is maturation factor (MF).

In another specific embodiment, the Notch signaling pathway is simulated to be mutated. The mutated Notch signaling pathway reduces Dkk secretion.

In another specific embodiment, the Wnt signaling pathway is simulated to be mutated. The mutated Wnt signaling pathway increases Dkk secretion.

The present invention is also directed to a method of determining a therapeutic regimen for the treatment of cancer with Dickkopf (Dkk) protein comprising: obtaining data to create a stem cell computer model for at least one signaling pathway involved in cancer stem cells, comprising a proliferated stem cell (SC) compartment and a differentiated cell (DC) compartment wherein the computer model integrates signals from the cancer stem cell environment based upon administration of at least a single dose of Dkk in vitro and/or in vivo; performing computer simulations using the stem cell computer model with data obtained from administration of the at least a single dose of Dkk to predict a treatment regimen for cancer by comparing effects of the at least a single dose of Dkk on cellular death.

In a specific embodiment, the cancer is selected from the group consisting of breast cancer, colon cancer, leukemia, and melanoma.

In another embodiment, Dkk is administered as a bolus, pulse or as a continuous administration.

In a specific embodiment, continuous administration of a low dose of Dick results in an increase in cellular death.

In a specific embodiment, bolus or pulse administration of a low dose of DKK results in the absence of cellular death.

In another embodiment, the at least a single dose is a low dose of Dkk.

In another embodiment, the low dose of Dkk induced SC proliferation.

In another embodiment, the at least a single dose is a high dose of Dkk.

In another embodiment, the high dose of Dkk results induced cell differentiation and cell death.

D. BRIEF DESCRIPTION OF THE DRAWINGS

The above objectives and advantages of the disclosed teachings will become more apparent by describing in detail preferred embodiment thereof with reference to the attached drawings in which.

E. DETAILED DESCRIPTION

The disclosed invention aims at untangling the crucial "switch factors", which determine the transition of CSCs from proliferation to differentiation. Our mathematical model describes the important molecular mechanisms that regulate stem cell fate-decision, that is the decision to selfrenew (proliferate) or to differentiate into a mature end cell.

The mathematical model for mammary stem cell fate-decision. The mathematical model was constructed by integrating the state-of-the art information about mammary SCs molecular pathways into the simplest possible description of the involved molecular mechanism. The model assumes two cell types: SCs and differentiated cells (DC). SCs are long-term cell population having potentially unlimited lifetime due to unlimited proliferation capacity. These cells self renew or undergo differentiation to DC. DC are short-term population incapable of proliferation. For simplicity, the model presented here assumes that the DC compartment comprises also the multi-potential progenitor cells, but this assumption can be easily relaxed.

It was assumed that Notch pathway and the Wnt canonical pathways are the most relevant pathways for the regulation of SCs proliferation and differentiation. In the present model, the Wnt canonical signaling pathway is described simplistically: Wnt ligand (ligand of the canonical pathway), Wnt target (LEF/TCF transcription factors) and Wnt inhibitor (Dkk secreted protein). Notch signaling cascade is represented by Notch receptor, DSL ligand and Notch target (Hes). In addition, density dependent inhibition is known to have an important role in epithelial homeostasis; it represses cell proliferation when E-cadherin junctions are formed. Accordingly, it was assumed that bound E-cadherins inhibit LEF/TCF activation. The number of bound E-cadherins on stem cell membrane depends on the amount of neighbor cells and their type (DC have larger expression of E-cadherin than SC).

Below are a listing of the exact assumptions made in the mathematical model.

Mammary SCs proliferation is irreversibly activated by the level of putative intracellular proliferation factors (PF) crossing a given threshold, $K_p$ n. If PF level is larger than the proliferation threshold ($K_p$), the SC passes through the restriction point and enters division. The variable PF is a simplified representation of several proteins known to promote cell cycle.

The production of PF is up-regulated by the intracellular LEF/TCF transcription factor, known to be activated by the Wnt canonical pathway. The activation of LEF/TCF is increased following the binding of Wnt to the Frizzled receptors. It is inhibited by Dkk, thus forming a negative feedback loop. The intracellular Wnt production is taken constant based on the assumption that it is in equilibrium with its degradation.

In contrast, the internal production of Dkk is up-regulated by LEF/TCF. In particular, the regulation of LEF/TCF depends also on Wnt and Dkk produced by other SCs. The current model also accounts for E-cadherin, which plays a pivotal role in the Wnt pathway and is involved in cell-cell contacts and growth inhibition. The induction of E-cadherins is negatively regulated by the Wnt pathway and positively regulated by Dkk. E-cadherins inhibit the activation of LEF/TCF following the binding of beta catenin to Ecadherins, thus preventing the binding of beta catenin to LEF/TCF. The degradation of the above mentioned factors is assumed to be linear.

In a similar way, mammary SCs differentiation is negatively regulated by extracellular signals that inhibit the activity of differentiation factors (DF). It is assumed that in quiescent, undifferentiated cells DF levels are below threshold (denoted $K_D$) and differentiation program is off. The production of maturation factors (MF) is downregulated by the intracellular Hes protein. The production rate of the Hes protein depends on the activation of Notch receptors following the binding of DSL ligands of the neighboring cells. The production of the Notch receptors is taken as constant while their degradation is down-regulated by LEF/TCF. The degradation of the Notch receptor is assumed to be non-linear.

From the above assumptions it appears that in the model LEF/TCF serve as the key proteins in SC fate division.

Non-negative Hill functions of the form:

$$f(x) = \frac{\mu \cdot a^m + v \cdot x^n}{a^m + x^m} \quad (1)$$

are used to express the influence of a protein in the system on the state of another protein. Note that these functions may provide a general description of more than one step in a pathway [Kirnasovsky O U et al, (9) in preparation]. These functions are monotonic, taking a sigmoid shape, bounded from above and below and having bounded derivatives. A Michaelis-Menten function is a particular case of a Hill function, when the sigmoid steepness (corresponding to the enzyme cooperativity) is equal to 1.

Figure 1:
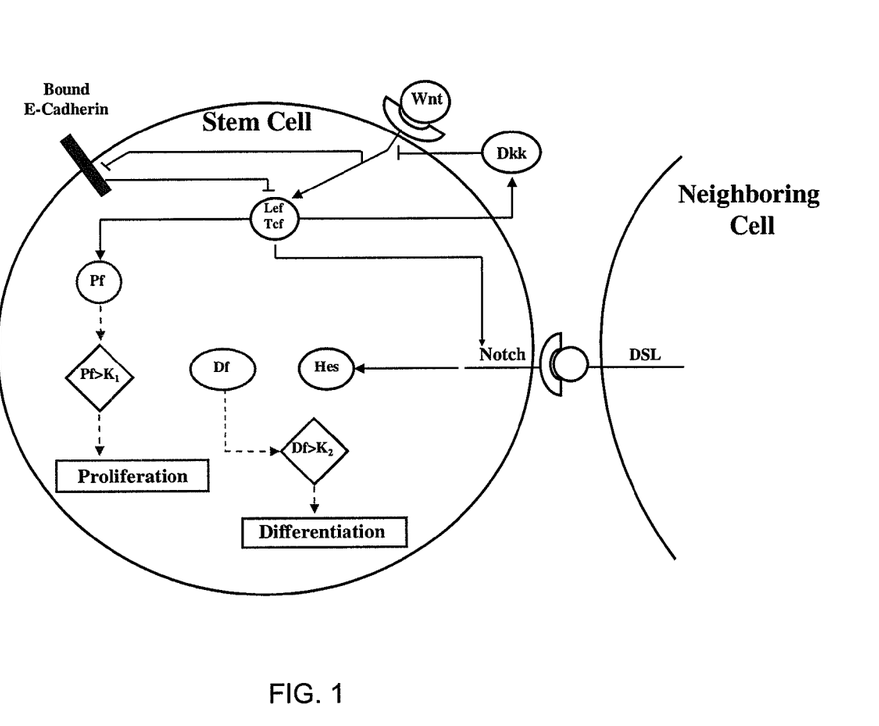
FIG. 1: Schematic description of the model describing the molecular mechanism underlying mammary SCs fate decision.

A schematic description of the model describing the molecular mechanism underlying mammary SC fate decision is depicted in FIG. 1.

The Wnt signaling pathway is activated by ligand binding to a receptor, promoting intracellular stimulation of LEF/TCF transcription complex, which increases the level of PF. Wnt signaling creates a negative feedback loop via Dick stimulation. E-cadherin mediated cell-cell adhesion further decreases PF cell level by inhibition of LEF/TCF activity. The Notch signaling pathway is activated by DSL ligand binding to receptor, which promotes expression of the Hes protein. Hes suppresses synthesis of DF in SCs. Wnt signaling inhibits E-cadherin transcription by Snail activation. Notch degradation is negatively regulated by Wnt signaling. The interaction between the above described signaling pathways determines SCs destiny.

The above description leads to the following dynamical system, formulated in terms of system of ordinary differential equations:

$$\dot{P} = f_P^\uparrow(L) - \mu_P \cdot P \quad (2)$$

$$\dot{M} = f_M^\downarrow(H) - \mu_M \cdot M \quad (3)$$

$$\dot{H} = f_H^\uparrow(\min(N,\delta)) - \mu_H \cdot H \quad (4)$$

$$\dot{N} = p_N - f_N^\downarrow(L) \cdot N \quad (5)$$

$$\dot{L} = f_L^\downarrow(E_{bound}) \cdot f_W^\downarrow(D_{total}) - \mu_L \cdot L \quad (6)$$

$$\dot{D} = f_D^\uparrow(L) - \mu_D \cdot D \quad (7)$$

$$\dot{E} = f_E^\downarrow(f_W^\downarrow(D)) - \mu_E \cdot E \quad (8)$$

Here P and M stand for intracellular PF and MF respectively. Other components of the described regulation system are represented by their key proteins:
H denotes the amount Hes-proteins;
N Notch-receptors on the cell surface;
δ Notch-ligands DSL;
L LEF/TCF-proteins;
D Dkk-proteins secreted by the cell;
$D_{total}$ the total Dkk that the cell "feels";
E E-cadherins;
$E_{bound}$ bound E-cadherins.

Additional parameters and functions used to describe the dynamics are:
$m_P$ linear degradation rate for P;
$f_P(L)$ production rate of P, which is increasing sigmoid in L;
$m_M$ linear degradation rate for M;
$f_M(H)$ production of M, which is decreasing sigmoid in H;
$m_H$ linear degradation rate for H;
$f_H(N)$ production rate of H, which is increasing sigmoid in N; see below a detailed description of the dependence of this function on the external signal, namely the amount of DSL receptors on the neighboring cells;
$p_N$ constant production of Notch receptors;
$f_N(L)$ degradation rate of Notch receptors, which is decreasing sigmoid in L;
$m_L$ linear degradation rate for L;
$f_W(D)$ production rate of L, which is decreasing sigmoid in D, this function represents the total signal of the Wnt pathway, including the influence of Dkk, but not the influence of E-cadherins (later we detail the dependence of this function on the external signals—Wnt and Dkk produced by other cells);
$f_L(E)$ the alteration of the production of L due to E-cadherin signal (later we detail the dependence of this function on the external signal—E-cadherins on the neighboring cells);
$m_D$ linear degradation rate for D;
$f_D(L)$ production rate of D, which is increasing Sigmoid in L;
$m_E$ linear degradation rate for E;
$f_E(f_W(D))$ production rate of E, which is increasing sigmoid in D (the superposition form of this functions stresses that the production of E is based on the same signal of the Wnt pathway, as the production of L).

The arrows in the functions denotation stand for the direction of the monotonicity. The parameters and the functions are determined by the micro-environment of the considered cell, and by the inner properties of this cell. It is noted that the equation describes the kinetics of E-cadherins in DCs by substituting LEF/TCF value by O.

To model the structure of the tissue we use a generalized Cellular Automata (CA), which is a well accepted formalism in biological modeling, describing the biological environment as a usually 2-dimensional grid in which each cell of the grid depicts a biological cell. In the current model the honeycomb grid is used on the torus surface with 800 cells. Each cell is allowed to exist only in given states (e.g. differentiated, cycling, dead etc.). Transition between states occurs according to predetermined rules and in certain discrete time steps. A current state of cell is determined by the relationship with its neighbors in the previous time step. In this mathematical model every automata cell in every time step is composed of the following variables. A SC committed to proliferation divides into two daughter cells following a cell-cycle of 12 hours. The daughter cells, containing the same amount of proteins as the mother cell, will randomly choose nonoccupied settling sites adjacent to the mother cell. In every step the levels of proteins in every cell and in the extracellular matrix are calculated. A differentiated cells survives in the tissue for a given time (200 hours) before dying, emptying a grid's cell.

Due to its complexity the model was analyzed numerically by computer simulations of the model (written in a computer language, like C++) under a large range of parameters for normal and cancer cells and different intervention scenarios.

Results

As shown in [Kirnasovsky O. U, et al Math. Model. Nat. Phenom. 3, 7, 78-89 (2008)], which is incorporated herein by reference in its entirety, analysis of the above mathematical model suggests that the Dkk signal in the Wnt pathway is a good candidate for being the Quorum Sensing counter that is for being the key molecule regulating the balance between SC proliferation and differentiation in mammary SCs.

Figure 2:
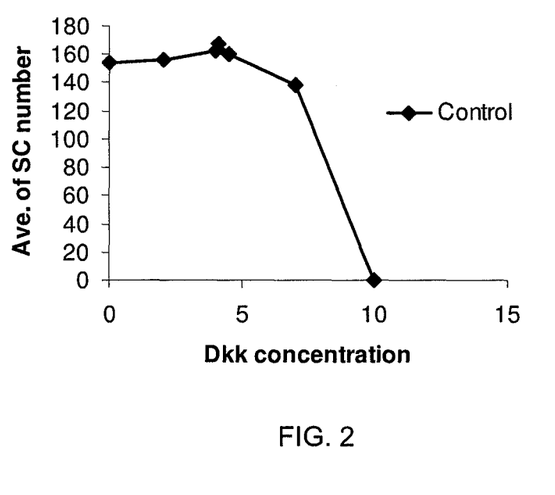
FIG. 2: Simulation of Dkk effect on SCs number. SCs were treated for 48 hours with different concentrations of Dkk. The simulations run for 3 months following Dkk treatment. Average of the SCs number survived in the last 3 days was calculated.
Figure 3:
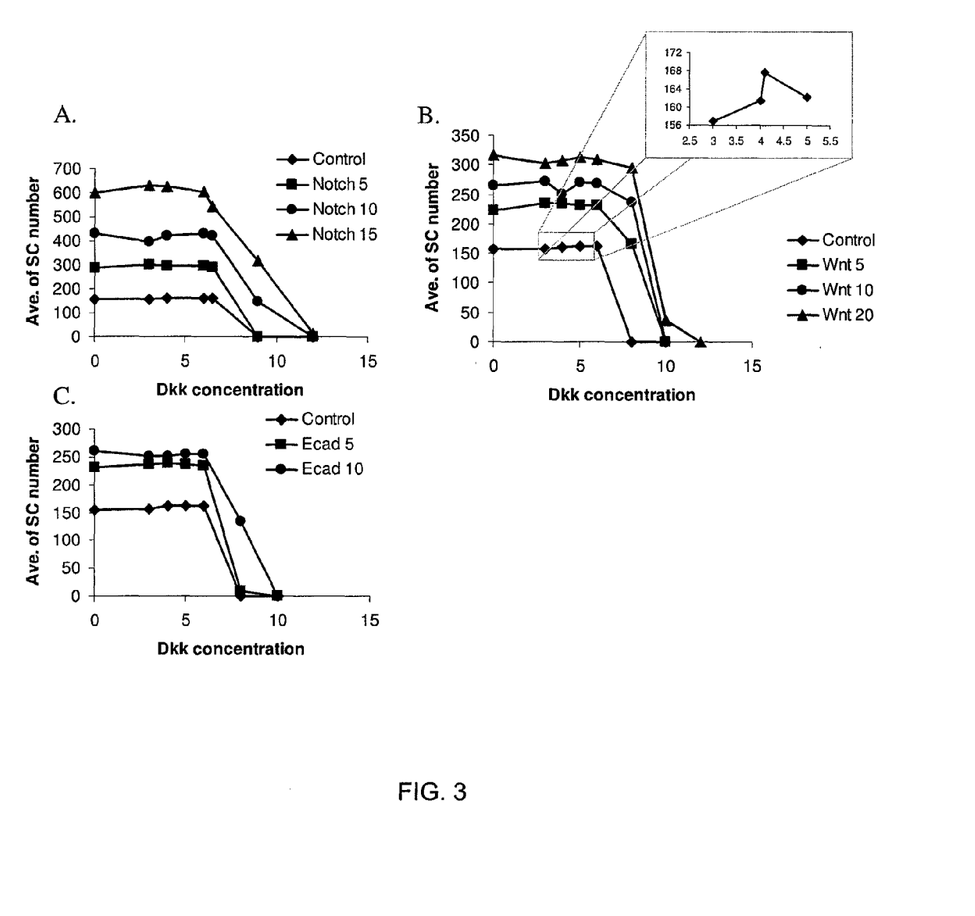
FIG. 3: Simulations of Dkk effect on SCs with Notch, Wnt and E-cadherin mutations. Control and mutated cells were treated for 48 h with different concentrations of Dkk. The simulations run for 3 months following Dkk treatment. Average of the SCs number survived in the last 3 days was calculated. expended view of SCs number as a function of Dkk concentration Between 3-5 arbitrary units.

In this work, the influence of Dkk on stem cells was numerically explored. To directly test the impact of Dkk on breast cancer stem cells, simulations were done in three ways:

Bolus, pulses and continuous administration of Dkk. Whereas bolus or pulse treatment of cancer stem cells with low concentrations (5-12 arbitrary units) of Dkk resulted in the absence of cellular death (not shown), continuous treatment of said cells resulted in a marked increase in cellular death at the same concentrations (FIG. 2). The results indicate that continuous treatment is more effective in eliminating cancer stem cells as compared to bolus or pulses treatments. Moreover, it is necessary to eliminate completely the cancer cell population in order to avoid recurrence of the disease.

Biphasic effect of ligands is common in biological systems. For example: low concentrations stimulate particular pathway whereas, high concentrations inhibit the pathway. In this regard, we examined the effect of Dkk on SCs number. The cells were treated with different concentrations of Dkk for 48 hours. The results indicate that treatment with Dkk (e.g., 4-5 in arbitrary units) increased SC number (of about 8%, P0.05, unpaired, two tailed t-test) whereas treatment with higher concentrations of Dkk (e.g., 10 in arbitrary units) induced cell differentiation and consequently cell death (FIG. 2). These results indicate that Dkk may act in a biphasic manner: in a specific range it facilitates SCs proliferation whereas above a certain threshold it facilitates differentiation.

Figure 4:
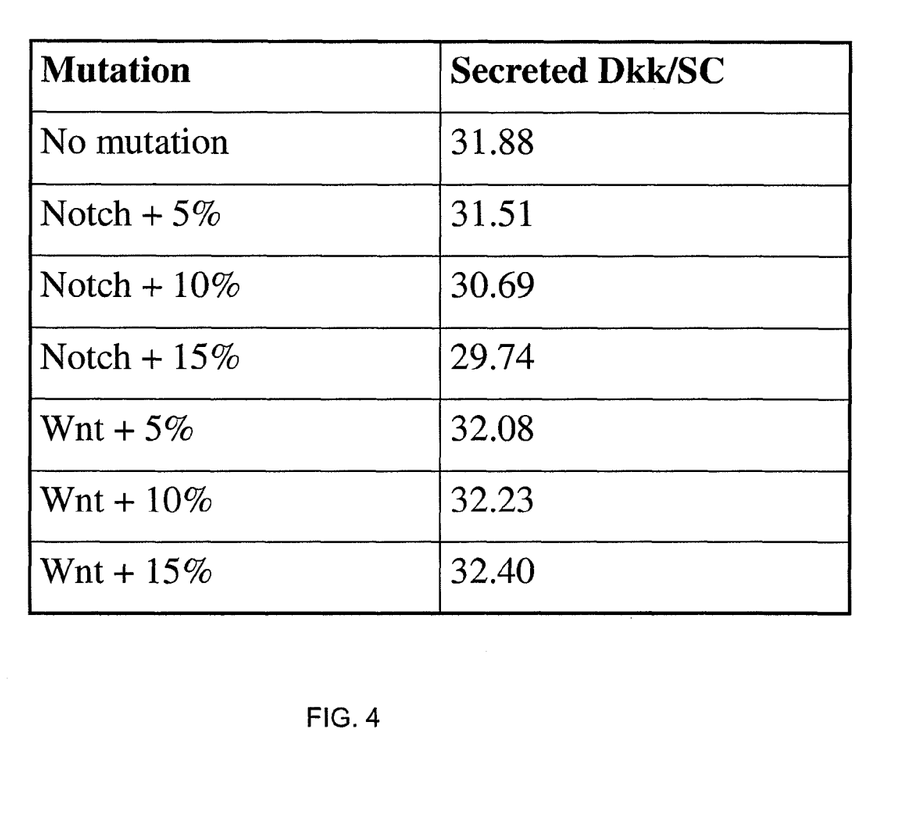
FIG. 4: Simulation of Dkk secretion by mutated cells. Average of Dkk seceretion was calculated in steady state condition.

Mutations in the signaling pathways governing self renewal and proliferation are usually common among mammary cancer stem cell. In order to examine the effect of Dkk on these mutations we simulated mutations in Notch (FIG. 4A), Wnt (FIG. 4B) and Ecadhefins (FIG. 4C) pathways resulting in increased cell proliferation. The mutated and control cells were treated in the simulation with different concentration of Dkk for 48 hour. The results indicate that mutated cells have a higher proliferation capacity compared with the control cells (FIG. 4). Moreover, it was shown that higher concentrations of Dkk are needed in order to induce differentiation and subsequent elimination of SCs.

In breast cancer metastases to the bones, Dkk secretion is up-regulated. We examined whether mutations in Notch and Wnt signaling pathways will increase Dkk secretion from the cells (FIG. 5). The results indicate that mutation in the Wnt pathway increases Dkk secretion whereas mutation in Notch signaling pathway reduces Dkk secretion.

In the present study a mathematical model is developed containing the major signaling pathways involved in stem cell regulation. The present inventors show by biological based mathematical simulations that addition of external Dkk that reaches a certain threshold of Dkk concentration in the stem cell micro-environment. In addition, as shown in U.S. Provisional Application Ser. No. 61/022,835, which is incorporated herein by reference in its entirety, Dkk acts as a quorum sensing "counter" results in a SCs and CSCs increases their differentiation capacity and subsequent elimination. In contrast, SCs and CSCs proliferation, rather than differentiation, was obtained, when specific concentrations of Dkk were used. The concentration of Dkk that induces proliferation is limited to a certain range of concentrations (lower than the threshold). By performing a calibration test the threshold above which Dkk concentration induces differentiation and the region of Dkk concentrations increase proliferation can be found.

The implications of Dkk on SCs and CSCs are broad. Dkk can affect the fate of these cells entering either differentiation proliferation. For example, when CSCs are exposed to Dkk concentrations higher then the threshold they are driven into differentiation. Once entered into the process the subsequent elimination of the CSCs is evident. Hence, the potential role of Dkk as an anticancer agent is clear. Dkk and its derivatives are useful as anticancer agents.

For using Dkk as an anticancer agent that affects CSCs a calibration assay is required. In the calibration different concentrations of Dkk the proliferation ability of these cells should be tested. A threshold concentration is then defined, above which the proliferation potential of CSCs decreases. A treatment with effective dose of Dkk is then suggested, where the Dkk concentration in the blood reaches the desired concentration level that inhibits proliferation.

Treatment with Dkk can be used for uncontrolled proliferation of cells, for cancerous and benign tumors and also stenosis and restenosis. Dkk affects CSCs that may give rise to a wide variety of other cancers, more specifically of epithelial tissues and more specifically of breast cancer.

Mutations in Notch, Wnt and E-cadherin are often found in many cancer types and in particular in mammary CSCs. In the present study CSCs are characterized by inducing these mutations. Three CSCs lines were generated each harboring a mutation in one of the genes. For each mutation the level of its effect was adjusted (e.g., 5% or 20%). The results obtained indicate that the average number of CSCs is higher then the average number of the normal (non-cancerous) stem cells. Therefore, the usefulness of treating CSCs with Dkk. This is where mutations in these genes occurred.

Moreover, Notch mutation significantly increases CSC number as compared to mutations in Wnt and E-cadherins. Hence, the use of Dkk to treat CSCs is more effective in cells where Notch is mutated.

Advanced stages of breast cancer are characterized by the formation of bone metastases (Rousselot N V, 2007, BJC). Cancer cell metastases secrete Dkk in order to induce osteolytic activation and inhibit osteoblasic activity. This special feature of the cancer cells can be explained by our simulations and results. In order to invade the bones the metastatic cancer cells secrete Dkk that influences osteolitic activity but not affect the CSCs. Therefore treatment metastasis, and especially of breast cancer, with Dkk may be highly effective.

The effect of Dkk on differentiation of SCs may have a prominent effect on tissue engineering and organ engineering. The ability to affect these cells to go through differentiation can be utilized when regeneration of tissues and organ is needed.

ABBREVIATIONS AND DEFINITIONS

Dkk: Dickkopf
DSL: Delta, Serrate, Lag-2
SCs: Stem cells
CSCs: Cancer stem cells
DC: Differentiated cells
MF: maturation factor Tissue and Organ engineering: The creation of living tissues for therapeutic purposes, natural or synthetic organs and tissues that can be implanted as fully functional units.

Side population: a small population within a tumor possesses a moltipotency phenotype.

Epithelial tissues: they form the covering of all body surfaces, line body cavities and hollow organs.

Wnt signaling pathway: the Wnt signal transduction pathway plays important roles during embryo development, regulating cell proliferation and survival of immature cells.

Notch signaling pathway: the Notch signaling pathway is well known for regulation proliferation and differentiation.

Tumor suppressor gene: is a gene that reduces the probability that a cell will turn into a tumor cell.

Apoptosis: it is one of the main types of programmed cell death.

Promoter hypermethylation: it is an important pathway for the repression of gene transcription.

Metalloproteases: a family of enzymes from the group of proteinases, classified by the nature of the most prominent functional group in their active site.

DSL: Notch signaling is induced following the binding of Delta, Serrate, Lag-2 (DSL) ligand on adjacent cells.

Switch factors: the factors that divert the cells from proliferation into differentiation.

Proliferation factors (PF): factors that induce cell proliferation.

Differentiation factors (DF): factors that induce cell differentiation.

Micro-environment: A close vicinity of the given cell, from which the cell can uptake different chemicals and signals from other cells and tissues.

Quorum sensing concept: a view, according to which the regulation of stern cell fate is achieved by intracellular communication between the stem cells and the tissue around the microenvironment.

REFERENCES

The following papers provide useful background information, for which they are incorporated herein by reference in their entirety, and are selectively referred to in this disclosure in brackets, e.g., [Aguilera O et al, Carcinogenesis, 28(9): 1877-84 (2007)].

The following papers provide useful background information, for which they are incorporated herein by reference in their entirety, and are selectively referred to in this disclosure in brackets, e.g., [Aguilera O et al, Carcinogenesis, 28(9): 1877-84 (2007)].

1. Aguilera O, Pena C, Garcia J M, Larriba M J, OrdOriez-Moran P, Navarro D, Barbachano A, Lopez de Silanes I, Ballestar E, Fraga M F, Esteller M, Gamallo C, Bonilla F, Gonzalez-Sancho J M, Munoz A. The Wnt antagonist DICKKOPF-1 gene is induced by 1alpha,25-dihydroxyvitamin D3 associated to the differentiation of human colon cancer cells. Carcinogenesis. 2007; 28(9):1877-84.
2. Agur Z., Daniel Y., Ginosar Y. The universal properties of stem cells as pinpointed by a simple discrete model. J. Math. Biol. 2002; 44, 79-86.
3. Agur Z., Kirnasovsky O. U., Levi L. High intercellular communication reduces carcinogenesis during tissue renewal: analysis of a theoretical model. (in preparation).
4. Berdnik D, TOrOk T, Gonzalez-Gaitan M, Knoblich J A. The endocytic protein alphaAdaptin is required for numb-mediated asymmetric cell division in *Drosophila*. Dev Cell. 2002; 3(2):221-31
5. Brennan K. R., Brown A. M. Wnt proteins in mammary development and cancer. J. Mammary Gland Biol. Neoplasia 2004; 9, 119-131
6. Gregory C A, Singh H, Perry A S, Prockop D J. The Wnt signaling inhibitor dickkopf-1 is required for reentry into the cell cycle of human adult stem cells from bone marrow. J Biol Chem. 2003; 278(30):28067-78.
7. Katoh M, Katoh M. NUMB is a break of WNT-Notch signaling cycle. Int J Mol Med. 2006; 18(3):517-21
8. Katoh M, Katoh M. Notch ligand, JAG1, is evolutionarily conserved target of canonical WNT signaling pathway in progenitor cells. Int J Mol Med. 2006; 17(4):681-5.
9. Kirnasovsky O. U., Kogan Y., Vainstein V., Agur Z. Investigation of tumour dynamics by mathematical modelling at the cellular level. (in preparation).
10. Kirnasovsky O. U., Kogan Y., and Agur Z. Analysis of a Mathematical Model for the Molecular Mechanism of Fate Decision in Mammary Stem Cells Math. Model. Nat. Phenom. 2008; Vol. 3, No. 7, pp. 78-89.
11. Kopper L, Hajchl M. Tumor stem cells. Pathol Oncol Res. 2004; 10(2):69-73.
12. Mikheev A M, Mikheeva S A, Liu B, Cohen P, Zarbl H. A functional genomics approach for the identification of putative tumor suppressor genes: Dickkopf-1 as suppressor of HeLa cell transformation. Carcinogenesis. 2004; 25(1):47-59.
13. Mikheev A M, Mikheeva S A, Rostomily R, Zarbl H. Dickkopf-1 activates cell death in MDA-MB435 melanoma cells. Biochem Biophys Res Commun. 2007; 352(3): 675-80.
14. Niehrs C. Function and biological roles of the Dickkopf family of Wnt modulators. Oncogene 2006; 25, 7469-7481.
15. Parkin D M, Bray F, Ferlay J, Pisani P. Global cancer statistics, 2002. CA Cancer J. Clin. 2005; 55(2): 74-108.
16. Reya T., Clevers H. Wnt signalling in stem cells and cancer. Nature 2005; 434, 843-850.
17. Sato H, Suzuki H, Toyota M, Nojima M, Maruyama R, Sasaki S, Takagi H, Sogabe Y, Sasaki Y, Idogawa M, Sonoda T, Mori M, Imai K, Tokino T, Shinomura Y. Frequent epigenetic inactivation of DICKKOPF family genes in human gastrointestinal tumors. Carcinogenesis. 2007; 28(12):2459-66.
18. Seo D C, Sung J M, Cho H J, Yi H, Seo K H, Choi I S, Kim D K, Kim J S, Abd El-Aty A M, Shin H C. Gene expression profiling of cancer stem cell in human lung adenocarcinoma A549 cells. Mol Cancer. 2007; 6(1):75
19. Woodward W A, Chen M S, Behbod F, Rosen J M. On mammary stem cells. J Cell Sci. 2005; 118 (Pt 16): 3585-94
20. Wu F., Stutzman A, Mo Y Y. Front Biosci. 2007; 12:4370-83.

What is claimed is:

1. A method of modulating normal stem cells or cancer stem cells involved in cancer selected from the group consisting of breast cancer, colon cancer, leukemia, and melanoma, the method comprising:
    creating a stem cell computer model for at least one signaling pathway involved in stem cell development, comprising a proliferating stem cell (SC) compartment and a differentiated cell (DC) compartment;
    simulating in a computer, an effect on the at least one signaling pathway of the stem cell computer model based upon data obtained from administration of at least a single dose of Dkk protein in vitro or in vivo;
    performing a calibration test based on the effect in the simulating step to determine a threshold Dkk concentration value above which administration of Dkk induces stem cell differentiation and a threshold Dkk concentration value below which administration of Dkk induces stem cell proliferation, wherein Dkk regulates stem cell differentiation and stem cell proliferation whereby a decrease in number of stem cells indicates stem cell differentiation and an increase in cellular growth indicates stem cell proliferation;
    inducing stem cell differentiation in normal or cancer stem cells with a dose of Dkk above the threshold Dkk concentration value indicative of stem cell differentiation, or inducing stem cell proliferation in normal or cancer stem cells with a dose of Dkk below the threshold Dkk concentration value indicative of stem cell proliferation.

2. The method of claim 1, wherein the at least one signaling pathway is selected from the group consisting of Wnt pathway and Notch pathway.

3. The method of claim 2, wherein the administration of a Wnt ligand activates the Wnt pathway by binding to a LRP transmembrane receptor.

4. The method of claim 3, wherein the binding of a Wnt ligand to a LRP transmembrane receptor activates LEF/TCF transcription complex upon the binding of beta catenin to LEF/TCF transcription complex.

5. The method of claim 4, wherein the LEF/TCF transcription complex up-regulates proliferation factors to induce the expression of Wnt target genes that induce cellular proliferation.

6. The method of claim 4, wherein the activation of LEF/TCF transcription complex up-regulates Dkk as a negative feedback loop.

7. The method of claim 6, wherein activation of LEF/TCF transcription complex is inhibited by Dkk to repress the expression of Wnt target genes to induce cellular differentiation.

8. The method of claim 4, wherein activation of LEF/TCF transcription complex is inhibited by E-cadherin.

9. The method of claim 2, wherein the binding of a Notch ligand activates the Notch pathway to up-regulate a Notch target.

10. The method of claim 9, wherein the Notch ligand is a DSL ligand and the Notch target is Hes.

11. The method of claim 10, wherein the binding of a DSL to a Notch receptor activates Hes.

12. The method of claim 11, wherein Hes suppresses synthesis of at least one differentiation factor (DF) in SC.

13. The method of claim 12, wherein the differentiation factor is maturation factor (MF).

14. The method of claim 2, wherein the Notch signaling pathway is simulated to be mutated.

15. The method of claim 14, wherein the mutated Notch signaling pathway reduces Dkk secretion.

16. The method of claim 2, wherein the Wnt signaling pathway is simulated to be mutated.

17. The method of claim 16, wherein the mutated Wnt signaling pathway increases Dkk secretion.

18. A method of determining a therapeutic regimen for the treatment of cancer selected from the group consisting of breast cancer, colon cancer, leukemia, and melanoma, with Dickkopf (Dkk) protein, the method comprising:
creating a stem cell computer model for at least one signaling pathway involved in cancer stem cell development, comprising a proliferating stem cell (SC) compartment and a differentiated cell (DC) compartment, wherein the computer model integrates signals from a cancer stem cell environment based upon administration of at least a single dose of Dkk in vitro and/or in vivo;
performing with a computer, computer simulations using the stem cell computer model based on data obtained from administration of the at least a single dose of Dkk, to predict a treatment regimen for cancer by comparing an effect of the at least a single dose of Dkk on cellular death;
performing a calibration test based on the effect in the simulations step to determine a threshold Dkk concentration value above which administration of Dkk induces stem cell differentiation and a threshold Dkk concentration value below which administration of Dkk induces stem cell proliferation, wherein Dkk regulates stem cell differentiation and stem cell proliferation whereby a decrease in number of stem cells indicates stem cell differentiation and an increase in cellular growth indicates stem cell proliferation;
selecting a treatment regimen for the treatment of cancer in which the effect of the at least a single dose of Dkk induces cellular differentiation.

19. The method of claim 18, wherein Dkk is administered as a bolus, pulse or as a continuous administration.

20. The method of claim 19, wherein continuous administration of a low dose of Dkk results in an increase in cellular death.

21. The method of claim 19, wherein bolus or pulse administration of a low dose of DKK results in the absence of cellular death.

22. The method of claim 18, wherein the at least a single dose is a low dose of Dkk.

23. The method of claim 22, wherein the low dose of Dkk induced SC proliferation.

24. The method of claim 18, wherein the at least a single dose is a high dose of Dkk.

25. The method of claim 24, wherein the high dose of Dkk results induced cell differentiation and cell death.

* * * * *